United States Patent
Kleven (10) Patent No.: US 8,834,455 B2
(45) Date of Patent: Sep. 16, 2014

(54) ATTACHMENT DEVICE FOR ATTACHING A RIGID BODY TO AN ARBITRARY MEDICAL INSTRUMENT

(75) Inventor: Atle Kleven, Trondheim (NO)

(73) Assignee: Sonowand AS, Trondheim (NO)

( * ) Notice: Subject to any disclaimer, the term of this patent is extended or adjusted under 35 U.S.C. 154(b) by 592 days.

(21) Appl. No.: 12/771,294

(22) Filed: Apr. 30, 2010

(65) Prior Publication Data

US 2011/0238043 A1    Sep. 29, 2011

(30) Foreign Application Priority Data

Mar. 25, 2010    (SE) ...................................... 1050285

(51) Int. Cl.
  *A61B 17/00*    (2006.01)
  *A61B 1/00*    (2006.01)

(52) U.S. Cl.
  CPC .................................. *A61B 1/00101* (2013.01)
  USPC ................................. 606/1; 600/102; 606/130

(58) Field of Classification Search
  USPC ......................................... 600/102; 248/74.3
  See application file for complete search history.

(56) References Cited

U.S. PATENT DOCUMENTS

| | | | | |
|---|---|---|---|---|
| 5,181,774 | A * | 1/1993 | Lane | 362/549 |
| 5,573,165 | A * | 11/1996 | Bloemer et al. | 224/523 |
| 7,100,808 | B2 * | 9/2006 | Hancock et al. | 224/547 |
| 7,392,967 | B2 * | 7/2008 | Liaw et al. | 248/218.4 |
| 2003/0225329 | A1 | 12/2003 | Rossner et al. | |
| 2004/0054489 | A1 | 3/2004 | Moctezuma De La Barrera et al. | |
| 2005/0045681 | A1 * | 3/2005 | Hancock et al. | 224/401 |
| 2007/0251356 | A1 * | 11/2007 | Tribby | 81/177.8 |
| 2008/0045972 | A1 | 2/2008 | Wagner et al. | |
| 2008/0154262 | A1 | 6/2008 | Brundobler et al. | |
| 2008/0164383 | A1 * | 7/2008 | Gunzburger | 248/74.3 |
| 2009/0247819 | A1 * | 10/2009 | Wilson et al. | 600/102 |
| 2009/0308823 | A1 * | 12/2009 | DiGasbarro | 211/85.13 |

FOREIGN PATENT DOCUMENTS

| | | |
|---|---|---|
| EP | 1889585 A1 | 2/2008 |
| WO | WO-03073951 A1 | 9/2003 |
| WO | WO-2004016178 | 2/2004 |

OTHER PUBLICATIONS

Extended European Search Report from corresponding European Application No. 10 161 611.8 dated Feb. 25, 2011, 5 pages.

* cited by examiner

*Primary Examiner* — Gary Jackson
*Assistant Examiner* — Jeffrey Lipitz
(74) *Attorney, Agent, or Firm* — Drinker Biddle & Reath LLP (57) ABSTRACT

The invention relates to an attachment adapter for attaching additional functions to a surgical tool. The attachment adapter provides a joint or a coupling between two instruments, e.g. a surgical tool and a navigation marker. The attachment adapter comprises an attachment body for attaching a surgical tool to the attachment adapter and a mounting seat with a mechanical coupling for fastening an add-on device to the attachment adapter. The attachment body comprises an elongate part adapted to receive the winding of a line and provided with at least two legs adapted to fit in an astride position on an elongate part of a surgical tool. It also comprises a line securing means adapted for securing a line, wound around the attachment body to join the attachment adapter to the surgical tool, in a locking position.

12 Claims, 7 Drawing Sheets

ATTACHMENT DEVICE FOR ATTACHING A RIGID BODY TO AN ARBITRARY MEDICAL INSTRUMENT

RELATED APPLICATIONS

This application claims priority under 35 U.S.C. §119 and/or §365 to Swedish Application No. SE 1050285-4, filed Mar. 25, 2010, the entire contents of which are incorporated herein by reference.

FIELD OF INVENTION

The present invention relates generally to medical instruments and to attachment devices for attaching additional functions to a medical instrument. More specifically, the present invention relates to an attachment adapter devised for achieving a joint or a coupling between two instruments.

BACKGROUND

In surgical operations in general there are in some situations need for joining two separate instruments to a combined functionality. For example, a surgical tool such as a guide tube to be inserted in the body of a patient may need to be fastened to a handle to allow a surgeon to hold the guide tube in a firm grip.

In brain surgery and other surgery, navigation enabling tools are used to assist the surgeon in positioning surgical instruments within the body of a patient. For example, ultrasound guided surgical tools are used together with positioning sensor navigation tools for enabling the surgeon to know the exact position of the tip of the surgical tool inside the body of a patient. Such a navigation tool is typically attached to an ultrasound probe or another surgical instrument.

Navigation tools for brain surgery typically include tracking markers, which enable the surgeon to control the coordinates of the tip of the surgical tool in space, notably out of sight inside a patient's body. The tracking markers may include active emitters and/or passive reflective markers that emit or reflect electromagnetic, magnetic or acoustic signals to one or more tracking devices. The tracking device is used to determine the position of the tracking markers and with calibration the actual position of the tip of a surgical tool attached to the navigation tool with the tracking markers. In the course of a surgical operation the surgeon often has a need to switch between different medical instruments that are connected to the navigation tool.

In order to be able to change between surgical instruments connected to the tracking marker and to enable sterilization of the surgical tools, there is a need for a flexible and easily attachable and releasable attachment device for adjoining medical instruments.

The attachment of a tracking marker to a surgical instrument is preferably a reversible attachment because of the need of using different types of navigation enabling tools and also because of the need for removal of the navigation tools for sterilization of the surgical tools.

PRIOR ART

Examples of prior art attachment devices are described in the following publications.

US20030225329 A1 shows a system for coupling surgical instruments to a medical navigation guidance system. The coupling system enables different sorts of markers and tracking markers to be attached to a surgical instrument. The coupling system comprises a fastener base, which is used to connect the markers and tracking markers to the surgical instrument. The fastener base is exchangeable, depending on the surgical instrument to which the tracking marker is to be attached. In one example the fastener base comprises a fastener body and a pair of clamping jaws for securing the fastener to an instrument by tightening the jaws by means of a worm screw. The fastener body has a mounting seat where a marker holder and a tracking marker can be attached and secured to prevent from rotation.

US2004054489A1 shows an adapter for attaching a tracking device to a surgical tool. The adapter has a cylinder-shaped interior opening where a surgical tool can be attached in a way that when the surgical tool is placed in the cylinder shaped interior so that the longitude axis of the cylinder coincides with the longitude axis of the surgical tool. The adapter also has a docking structure for attachment of a tracking device.

EP1889585A1 shows an adapter for attaching a surgical tool to a tracking device. The adapter has a self aligning coupling mechanism, clamp-like structure with flat surfaces in contact with the surgical tool.

WO2004/016178A2 shows interaction of a surgical tool and a marker system with an attachment with a switch mechanism.

US28154262A1 shows a system for guiding medical objects, for example a needle and comprises a fixation clamp with a screw fastener mechanism which can be used to attach the needle to a navigation element.

OBJECT OF THE INVENTION

General Object

The general object of the invention is to solve the problem of providing an attachment device for detachable mechanical interconnection of an add-on device to a medical tool.

A more specific object and a partial problem are to provide an attachment adapter for attaching a rigid body of an add-on-device, such as a surgery navigation tool, to a surgical tool.

SUMMARY OF THE INVENTION

In accordance with the present invention the object is fulfilled and the problem is solved 3o by an attachment adapter that is configured with a tool attachment body for attaching a surgical tool to the attachment adapter and a mounting seat for fastening an add-on device to the attachment adapter. The attachment body of the attachment adapter comprises a saddle piece, i.e. an elongate part adapted to receive the winding of a line and provided with at least two legs adapted to fit in an astride position on an elongate part of a surgical tool. The attachment body also comprises a line securing means adapted for securing a line, wound around the attachment body to join the attachment adapter to the surgical tool, in a locking position. Preferably, the attachment body comprises at least two pairs of legs preferably positioned at the respective ends of the attachment body.

The attachment adapter of the invention enables surgical instruments to be attached to a functional device or another medical instrument in a simple manner. Once mounted in a correct manner the attachment adapter safely and rigidly ties the tools together. Another effect and advantage is that the attachment adapter is easy to handle and flexible to use in a surgical situation. Moreover, the attachment device is easily removed and reattached before, during or after surgery.

In one aspect the invention relates to an attachment adapter for a surgical tool. The attachment adapter provides a joint or a coupling between two instruments, e.g. a surgical tool and a navigation marker. The attachment adapter comprises an attachment body for attaching a surgical tool to the attachment adapter and a mounting seat with a mechanical coupling for fastening an add-on device to the attachment adapter. The attachment body comprises an elongate part adapted to receive the winding of a line and provided with at least two legs adapted to fit in an astride position on an elongate part of a surgical tool. It also comprises a line securing means adapted for securing a line, wound around the attachment body to join the attachment adapter to the surgical tool, in a locking position.

BRIEF DESCRIPTION OF THE FIGURES

The present invention will be further explained below with reference to the accompanying drawings, in which.

DETAILED DESCRIPTION OF THE INVENTION

Attachment Adapter

The present invention concerns an attachment adapter for attachment of an add-on device or functional device to a surgical tool or other medical instrument. The add-on device is for example a navigation tool such as a tracking marker or another functional device or even an aesthetic device. The invention comprises a fastening interface between the surgical tool and the functional device that provides add-on functionality to the surgical tool.

Figure 1A:
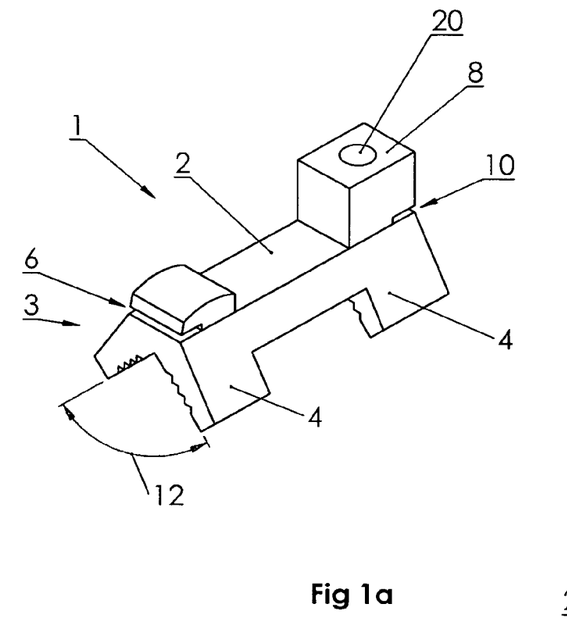
FIGS. 1a-b show exemplifying embodiments of an attachment adapter according to the invention where the mounting seat is rigidly coupled to the attachment body.
Figure 1B:
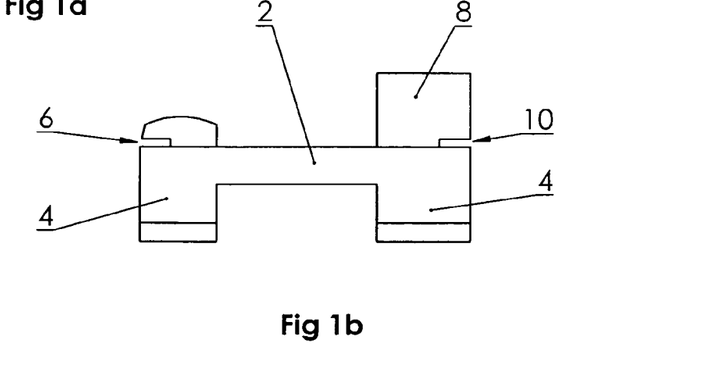

FIG. 1A and FIG. 1B show an exemplifying embodiment of the invention. The attachment adapter 1 has a tool fastening means 3 in the shape of a saddle piece with an attachment body 2 and four legs 4. The legs 4 are configured in pairs at the respective ends of the elongated attachment body 2 making up the "saddle". The saddle piece is configured for fitting the attachment adapter to an elongate part of a first medical instrument in a saddling position with the legs sitting astride the medical instrument.

At one end of the attachment body 2 (to the right in FIG. 1A) there is a mounting seat 8 for mounting an add-on device to the adapter. In the shown embodiment the mounting seat 8 is rigidly coupled to the attachment body 2 by virtue of being manufactured in one piece.

At the other end of the attachment body 2 (to the left in FIG. 1B) there is a first line securing means 6 devised for securing a line used to fasten the attachment adapter to the first medical instrument in accordance with the invention. In the shown embodiment there is a second, optional line securing means 10 configured close to the mounting seat 8. The attachment body according to the invention is equipped with at least one line securing means 6, 10. The line securing means 6, 10 may be located at any part of the elongated attachment body 2.

Figure 5A:
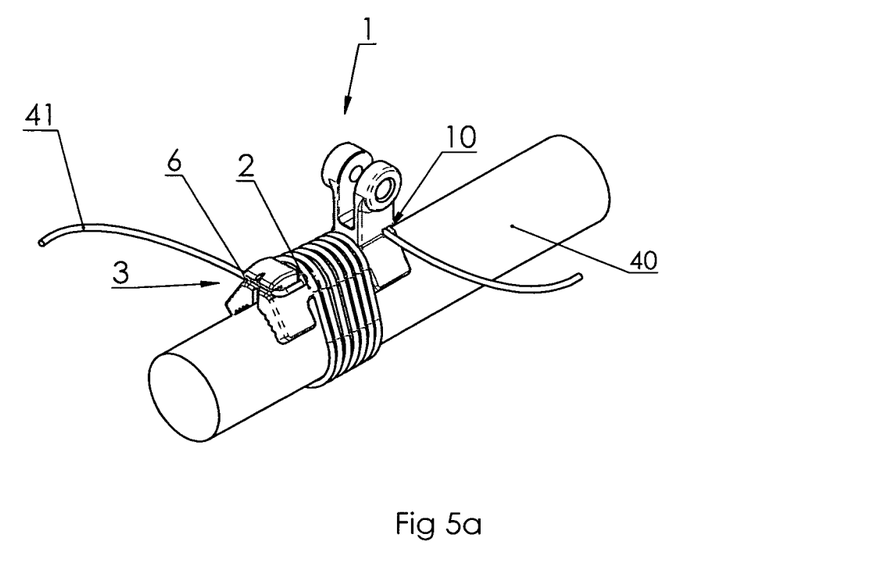
FIGS. 5a-b show two different exemplifying embodiments of the inventive attachment adapter fastened to an elongate part of a medical instrument.
Figure 5B:
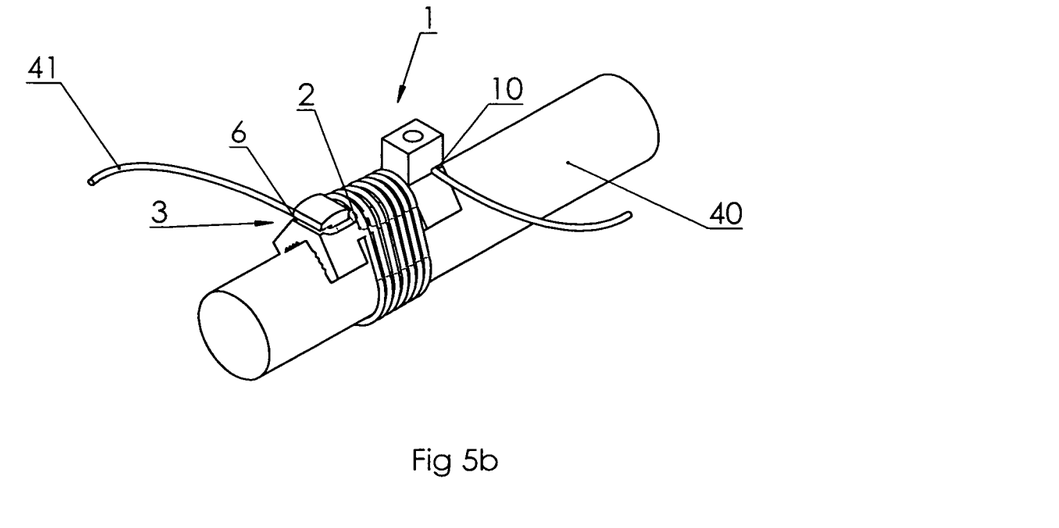

FIG. 5A and FIG. 5B shows two different embodiments of the attachment adapter fastened to a tool 40. In operation, a user fits the attachment adapter 1 to a tool 40 by saddling the attachment adapter over an elongate part of the tool 40. The tool fastening means 3 is then secured to the tool 40 by winding a line 41, for example an elastic cord, a medical grade silicon line or biocompatible silicon tubing or a suture thread, around the saddle back of the attachment body 2 and the surgical tool 40. After winding, the line 41 is secured to a line securing means 6, 10.

Attaching an Add-on Device—Angular Adjustment

Referring to FIG. 1A and FIG. 1B, the mounting seat 8 of the shown embodiment of the attachment adapter is provided with a mechanical coupling 20, i.e. a mechanical device that serves to connect the attachment adapter 1 to an add-on device. In the shown embodiment the mechanical coupling 20 is a socket for receiving a fittingly shaped insert (not shown) provided at the add-on device. The shown socket 20 has the shape of a drill hole with a typical diameter in the range of 3-6 mm. A drill hole formed socket allows adjustment of the angular position of the add-on device in relation to the surgical tool around a pivot axis through the drill hole and a cylindrically shaped insert. Other cross-sectional shapes of the socket and the insert are conceivable, for example any suitable polygon or splines, but would not allow angular adjustment. In one embodiment the additional instrument is configured to be fastened to the socket with click-on means.

In another embodiment the mechanical coupling 20 may for instance be a peg or protrusion, which is to be received in a fittingly shaped socket of the add-on device. Other possible mechanical couplings 20 include VELCRO, a fastener formed of hooks and loops, and bayonet mount, snap lock, tape or hook devices.

The mounting seat 8 has, in different embodiments of the attachment adapter, different shapes and configurations selected depending on which instrument that is to be mounted. In order to obtain further degrees of freedom in the relative position of the attached instruments some embodiments of the invention also comprises further angular adjustment means.

Figure 2:
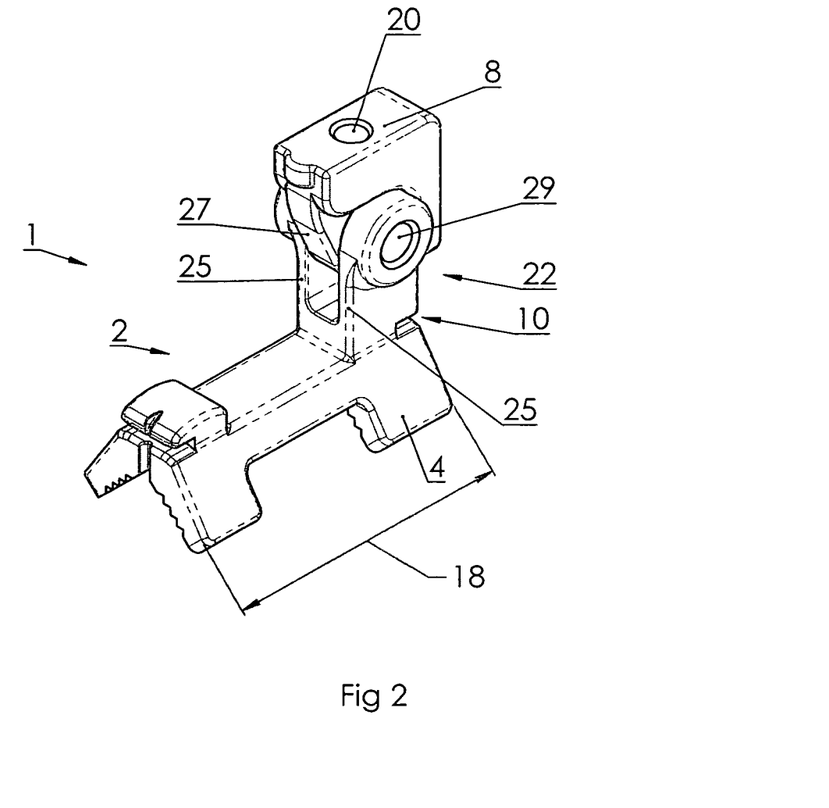
FIGS. 2 and 3a-b shows exemplifying embodiments of an attachment adapter where the mounting seat is fastened to the attachment body by angular adjustment means with a double flange.
Figure 4:
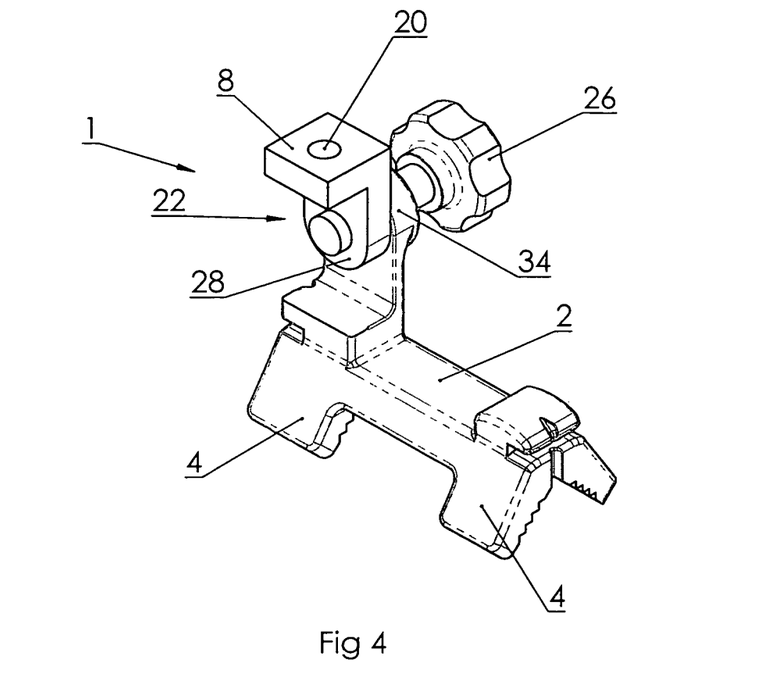
FIG. 4 shows exemplifying embodiments of an attachment adapter where the mounting seat is fastened to the attachment body by angular adjustment means with a single flange

In the embodiment shown in FIG. 2 and FIG. 4 a mounting seat 8 as explained above is fastened to the attachment body 2 by means of an angular adjustment means 22.

In FIG. 2 the angular adjustment means 22 comprises a double flange coupling. In the double flange coupling, two parallel flanges 25 rigidly coupled to the attachment body 2 and a single flange 27 rigidly coupled to the mounting seat 8 are joined by means of an adjustable locking screw 29. In the shown variant of this embodiment the mounting seat 8 with the single flange 27 is substantially T-shaped.

FIG. 4 shows a variant of the previous function in an embodiment where the angular adjustment means 22 comprises a single flange 34 rigidly coupled to the attachment body 2 and a single flange 28 rigidly coupled to the mounting seat 8. The flanges 28 and 34 are similarly joined by means of an adjustable locking screw 26. In the variant shown in FIG. 4 the mounting seat 8 with the flange 28 is L-shaped.

In embodiments such as those shown in FIGS. 2 and 4 angular adjustment is enabled around a first pivot axis provided by the mechanical coupling 20 and around a second pivot axis provided by the locking screw 26, 29. In this way the mechanical coupling 20 allows the add-on device to rotate horizontally relative to the elongated axis of the attachment body 2 (and surgical tool) while simultaneously the angular adjustment means 22 allows the add-on device to rotate vertically relative to the elongated axis of the attachment body 2.

The Attachment Body

The attachment body 2 is configured to follow the shape of an elongate part of a surgical tool to be attached. It is constructed/designed in a way that enables it to be attached to any surgical tool of preferably circular or oval longitudinal shape with diameter in the range of 2 mm-35 mm. The attachment body 2 is with its legs 4 adapted to fit in a saddle position on a part of a surgical tool with a cross-section that is for example circular, oval or polygonal. As explained above the elongated attachment body 2 is adapted to receive the winding of a line, and in preferred embodiments adapted to lines in the shape of an elastic cord (for example a biocompatible silicon cord). The attachment body 2 has a first line securing means 6 at one end and a possibly a second line securing means 10 at the other end close to the mounting seat 8. To mount the attachment adapter to a surgical tool a line is wound over the length of attachment body 2 and the surgical tool beneath it. The line is then secured to the first and/or second line securing means 6, 10. The elongate part of the attachment body 2 has a length 18 dimensioned to allow a line of a matching line dimension to be wound about 5-30 mm loops, preferably 4-6 mm loops along the body for a rigid attachment. The length 18 of the elongated attachment body is typically 10-60 mm. The elongated attachment body 2 may further comprises a line recess along the body of the attachment body 2 to allow for a part of the line to fit tightly under the winding.

Line Securing Means

The first line securing means 6 is preferably located at one end of the elongated attachment body 2 and is formed as a recess or cleavage which is used to secure the line. The line securing recess has a width 14 of 0.5-1.5 mm dimensioned in relation to an intended line so that the line will fit in the cleavage with a press-fit. For a elastic cord the width 14 would be in the range of 0.5-2.5 mm.

Figure 3A:
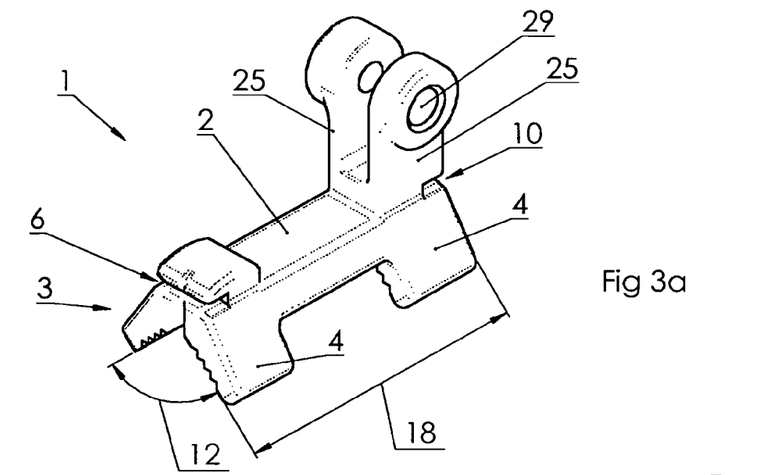
Figure 3B:
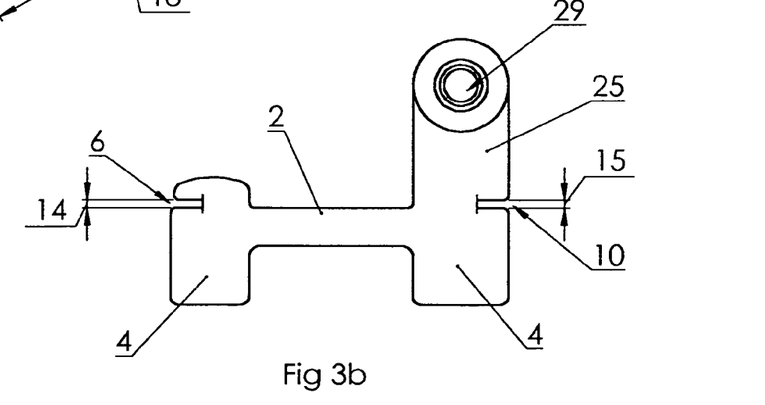

In an embodiment of the invention the elongated attachment body 2 also comprises an optional second line securing means 10 (see for example FIGS. 1-3). The second line securing means 10 is located at the opposite end of the elongated attachment body 2 in relation to the first line securing means 6 and is used to additionally secure the line. The second line securing means 10 comprises a cleavage in the structure similarly to the first line securing means 6, the second line securing means typically has a different orientation than the first line securing means. The cleavage of the second line securing means 10 has a width 15 of 0.3-1.0 mm so that the line will fit in the cleavage with a press-fit.

Legs

Figure 6A:
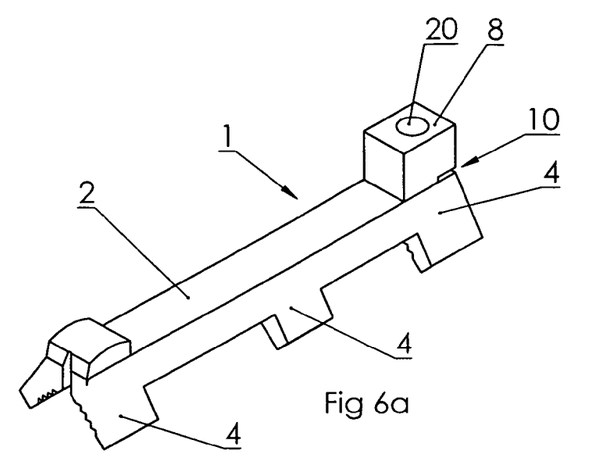
FIGS. 6a-c show different exemplifying embodiments of the attachment adapter according to the invention with different variants of a saddle piece for fitting the attachment adapter to an elongate part of an instrument.
Figure 6B:
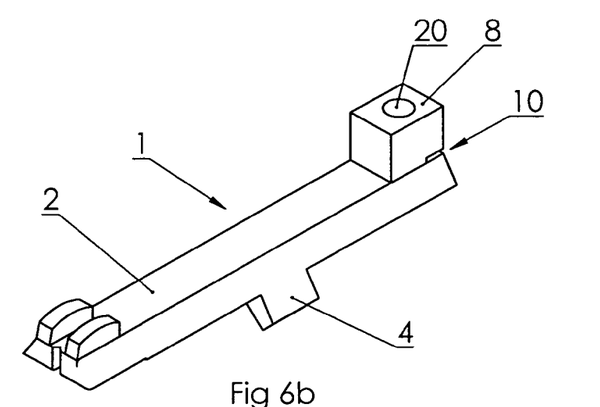
Figure 6C:
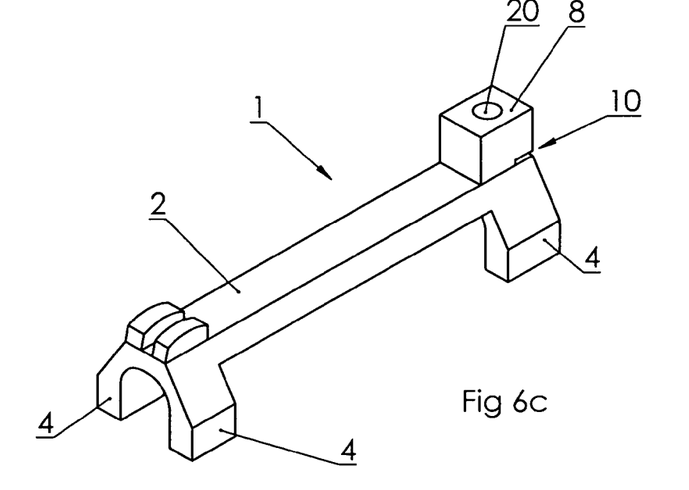

FIGS. 6*a-c* show different embodiments of the attachment adapter with different configurations of the legs 4. The elongated attachment body 2 is provided with at least one pair of legs 4. In different embodiment of the invention the legs 4 are spread out along the elongated attachment body 2 or aligned in pairs. Preferably, the attachment body comprises at least two pairs of legs preferably positioned at the respective ends of the attachment body. The placement of the legs 4 should allow the winding of a line around the elongated attachment body 2.

In a preferred embodiment, as shown in FIGS. 1-5 and 6*a-b*, the legs in a pair of legs are placed in V-shape in relation to one another. The angle 12 between the legs is in one example 45° (see for example FIG. 1*a-b*). The legs can also have a different angles or configurations for example U-shaped, see FIG. 6*c*. The lengths of the legs 4 are typically in the range of 2-10 mm in order to fit to standard dimensions of surgical instruments. The position of the legs 4 contribute to stabilize the surgical tool which is to be attached.

In one embodiment the inside of the legs 4 of the attachment adapter 1, i.e. the side designed to face the surgical tool, may be lined with a high friction material such as silicon or rubber. In this way elevated rigidity and precision in the positioning of the attachment adapter 1, and thus an attached navigation device or other add-on, to the surgical tool is achieved.

Materials of the Attachment Adapter

The attachment adapter 1 is made from a material which can be sterilized. It can be of interest to manufacture the attachment adapter 1 from a material capable of being sterilized several times, alternatively the adapter is made to be discarded after use. Materials suitable for the attachment adapter 1 according to the invention are plastics that are stable and surgically acceptable for example; polyetheretherketone (PEEK), carbon fiber reinforced PEEK, polysulfone, polycarbonate, nylon, among others. Suitable metals are surgical stainless steel, titanium, tungsten carbide.

The Securing Line

The line 41 used to attach the surgical tool to the attachment adapter 1 is preferably an elastic cord, line or band. The cord needs to be sufficiently strong to withstand the weight of the surgical tool and an additional instrument. The cord preferably has sufficient tension strength to allow a tight wounding of the surgical tool to the attachment adapter. The thread preferable has a diameter of 0.5-2.5 mm. In one embodiment of the invention the securing line or elastic cord is a biocompatible silicon tubing.

Usage Example

The attachment adapter 1 according to the invention is for example used for coupling of a navigation guidance system, for example a stereotactic navigation system, to a surgical tool. The navigation guidance system uses a computer and a tracking sensors or tracking markers for example a tracking markers with attached reflective spheres for determining position. The attachment adapter 1 according to the invention allows the tracking markers to be coupled to the mounting seat 8 of the adapter. The tracking markers allows for determining the exact position of the surgical tool inside the patient. Examples of surgical tools used together with the attachment adapter according to the invention are pointers, scalpels and forceps among others.

The attachment adapter 1 according to the invention enables the surgeon to use any surgical instrument of choice as a navigator to generate stereotactic imagery based on intra-operative images or preoperative images to guide the surgical procedure based in image information.

The attachment needs to be stabile and rigid because of the high precision that is needed for the surgical tools.

The attachment adapter 1 according to the invention is easily connected and disconnected to and from the surgical tool, and to and from the add-on device, e.g. tracking markers. The simple attachment and removal of the attachment adapter 1 is important because the tracking marker or the surgical tool both might be changed during surgery. Also, the surgical tool has to be detached for sterilization between different surgery operations.

By using this attachment adapter 1 according to the invention, the surgical tool and add-on devices can be connected to each other in a reversible way, allowing the surgeon to switch between instruments and also allowing for sterilization of the separate parts. The fastening means according to the invention is rigid due to the friction of the line towards the surgery tool and the attachment adapter 1, it is also easy for the surgeon to attach or detach the line with gloves on during surgery.

The invention claimed is:

1. An attachment adapter for an elongate surgical tool, comprising:
    an attachment body for attaching the surgical tool to the attachment adapter; and
    a mounting seat with a mechanical coupling for fastening an add-on device to the attachment adapter,
    wherein the attachment body comprises:
        an elongate part adapted to receive a plurality of windings of an attachment line completely around said elongate part and the surgical tool, wherein said elongate part has a long axis;
        at least two legs adapted to fit in an astride position on an elongate part of the surgical tool; and
        line securing members at opposite ends of the long axis of said elongate part of the attachment body, each member having a jam slot dimensioned in relation to said attachment line so that said attachment line securely press fits within said jam slot, permitting said attachment line to be press fit into one jam slot, whereafter said attachment line is wound multiple times around the elongate part of the attachment body and the surgical tool, whereafter the remaining portion of said attachment line is press fit into the other jam slot, thereby locking the attachment body securely in alignment astride the elongate surgical tool.

2. The attachment adapter according to claim 1, wherein the attachment body comprises at least two pairs of legs positioned at the respective ends of the attachment body.

3. The attachment adapter according to claim 2, wherein the legs of a leg pair are separated at an angle of 45°.

4. The attachment adapter according to claim 1, further comprising an angular adjustment member that enables angular adjustment of the mounting seat in relation to the attachment body, thereby enabling angular adjustment of an add-on device in relation to a surgical tool attached to the attachment adapter.

5. The attachment adapter according to claim 4, wherein the angular adjustment member is coupled to the attachment body with a single flange coupling.

6. The attachment adapter according to claim 4, wherein the angular adjustment member is attached to the attachment body with a double flange coupling.

7. The attachment adapter according to claim 1, wherein the mechanical coupling is a socket.

8. The attachment adapter according to claim 1, wherein the mechanical coupling is adapted for fastening the add-on device with a click-on member.

9. The attachment adapter according to claim 1, comprising an elastic cord.

10. The attachment adapter according to claim 1, wherein a recess or cleavage forming the jam slot of the line securing members is recessed in the longitudinal direction from an end of the attachment body.

11. A kit comprising:
    a navigation guidance system;
    a surgical tool; and
    an attachment adaptor,
    wherein the attachment adaptor comprises:
        an attachment body for attaching the surgical tool to the attachment adapter; and
        a mounting seat with a mechanical coupling for fastening the navigation guidance system to the attachment adapter,
        wherein the attachment body comprises:
            an elongate part adapted to receive winding of an attachment line completely around the elongate part and the surgical tool, wherein said elongate part has a long axis;
            at least two legs adapted to fit in an astride position on an elongate part of the surgical tool; and
            line securing members at opposite ends of the long axis of said elongate part of the attachment body, each member having a jam slot dimensioned in relation to said attachment line so that said attachment line securely press fits within said jam slot, permitting said attachment line to be press fit into one jam slot, whereafter said attachment line is wound multiple times around the elongate part of the attachment body and the surgical tool, whereafter the remaining portion of said attachment line is press fit into the other jam slot, thereby locking the attachment body securely in alignment astride the elongate surgical tool.

12. A surgical tool attachment system comprising: an elongate surgical tool, an attachment line, and an attachment adapter for the surgical tool, comprising:
    an attachment body for attaching the surgical tool to the attachment adapter; and
    a mounting seat with a mechanical coupling for fastening an add-on device to the attachment adapter;
    wherein the attachment body comprises:
    an elongate part adapted to receive a plurality of windings of said line completely around said elongate part and the surgical tool, wherein said elongate part has a long axis;
    at least two legs adapted to fit in an astride position on an elongate part of the surgical tool; and
    line securing members at opposite ends of the long axis of said elongate part of the attachment body, each member having a jam slot dimensioned in relation to said line so that said line securely press fits within said jam slot, permitting the line to be press fit into one jam slot, whereafter the line is wound multiple times around the elongate part of the attachment body and the surgical tool, whereafter the remaining line is press fit into the other jam slot, thereby locking the attachment body securely in alignment astride the elongate surgical tool.

* * * * *